United States Patent
Rosenbloom

(10) Patent No.: US 7,435,725 B2
(45) Date of Patent: *Oct. 14, 2008

(54) ORAL COMPOSITIONS AND METHODS FOR PREVENTION, REDUCTION AND TREATMENT OF RADIATION INJURY

(75) Inventor: Richard A. Rosenbloom, Elkins Park, PA (US)

(73) Assignee: The Quigly Corporation, Doylestown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/045,790

(22) Filed: Jan. 14, 2002

(65) Prior Publication Data

US 2003/0103954 A1   Jun. 5, 2003

Related U.S. Application Data

(63) Continuation-in-part of application No. 09/993,003, filed on Nov. 6, 2001.

(51) Int. Cl.
```
A61K 31/59    (2006.01)
A61K 31/355   (2006.01)
A61K 31/20    (2006.01)
A61K 31/07    (2006.01)
A61K 8/00     (2006.01)
A61K 8/18     (2006.01)
A61Q 17/04    (2006.01)
```
(52) U.S. Cl. ............... 514/167; 514/458; 514/558; 514/725; 424/59
(58) Field of Classification Search ............ 424/59, 424/60; 514/167, 168, 170, 458, 558, 725
See application file for complete search history.

(56) References Cited

U.S. PATENT DOCUMENTS

| | | | |
|---|---|---|---|
| 4,147,795 A | 4/1979 | Sarges | |
| 4,210,667 A | 7/1980 | Sarges et al. | |
| 4,232,040 A | 11/1980 | Waterbury | |
| 4,250,097 A | 2/1981 | Pfister | |
| 4,617,187 A | 10/1986 | Okuyama et al. | 424/94.1 |
| 4,627,973 A | 12/1986 | Moran et al. | |
| 4,822,816 A | 4/1989 | Markham | |
| 5,011,840 A | 4/1991 | Sarges et al. | |
| 5,070,085 A | 12/1991 | Markham | |
| 5,141,741 A * | 8/1992 | Ishida et al. | 424/59 |
| 5,446,034 A | 8/1995 | Bretting et al. | |
| 5,550,249 A | 8/1996 | Della Valle et al. | |
| 5,561,110 A | 10/1996 | Michaelis et al. | |
| 5,571,441 A | 11/1996 | Andon et al. | 252/1 |
| 5,595,982 A | 1/1997 | Harless | |
| 5,614,224 A | 3/1997 | Womack | |
| 5,648,083 A | 7/1997 | Blieszner et al. | |
| 5,650,137 A * | 7/1997 | Nguyen et al. | 424/59 |
| 5,665,360 A | 9/1997 | Mann | |
| 5,686,082 A | 11/1997 | N'Guyen | |
| 5,709,868 A | 1/1998 | Perricone | |
| 5,776,460 A * | 7/1998 | Kim et al. | |
| 5,804,168 A | 9/1998 | Murad | 424/59 |
| 5,824,666 A | 10/1998 | Deckner et al. | |
| 5,840,736 A | 11/1998 | Zelle et al. | |
| 5,866,578 A | 2/1999 | Mylari et al. | |
| 5,872,140 A | 2/1999 | Hesse et al. | |
| 5,876,737 A | 3/1999 | Schonrock et al. | |
| 5,883,086 A | 3/1999 | Craft | |
| 5,895,652 A | 4/1999 | Giampapa et al. | |
| 5,922,335 A | 7/1999 | Ptchelintsev | |
| 5,948,443 A | 9/1999 | Riley et al. | |
| 5,952,391 A | 9/1999 | Gers-Barlag et al. | |
| 5,958,379 A | 9/1999 | Regenold et al. | |
| 5,972,359 A | 10/1999 | Sine et al. | |
| 5,972,999 A | 10/1999 | Murad | |
| 5,976,568 A | 11/1999 | Riley | |

(Continued)

FOREIGN PATENT DOCUMENTS

EP   0511895   11/1992

(Continued)

OTHER PUBLICATIONS

Hardman et al. "Goodman & Gilman's The Pharmaceutical Basis of Therapeutics" (9th ed, 1996) p. 51 and 57-58.*

(Continued)

*Primary Examiner*—San-ming Hui
(74) *Attorney, Agent, or Firm*—Knoble, Yoshida & Dunleavy LLC

(57) ABSTRACT

An oral composition for the prevention, reduction or treatment of radiation injury including one or more compounds that regulates cell differentiation and/or cell proliferation, and one or more antioxidants, optionally formulated in a pharmaceutically acceptable carrier for an oral composition. The composition of the present invention may further include optional ingredients such as flavonoids, flavonoid derivatives, selenium, selenium compounds, anti-inflammatories, organic germanium, Korean ginseng, American ginseng, Siberian ginseng and B-complex vitamins. A method for the administration of an oral composition for the purpose of preventing, reducing or treating radiation injury involves orally administering an effective amount of a composition including one or more compounds that regulates cell differentiation and/or cell proliferation, and one or more antioxidants to a person before, during or after radiation exposure. The compositions and methods can be employed to prevent, reduce or treat radiation injury caused by a wide variety of types of radiation exposure.

26 Claims, No Drawings

U.S. PATENT DOCUMENTS

| | | | |
|---|---|---|---|
| 5,976,579 | A | 11/1999 | McLean |
| 5,981,594 | A | 11/1999 | Okamoto et al. |
| 5,998,394 | A | 12/1999 | Voorhees et al. ............ 514/167 |
| 6,048,886 | A | 4/2000 | Neigut |
| 6,051,602 | A * | 4/2000 | Bissett ....................... 514/456 |
| 6,054,128 | A | 4/2000 | Wakat |
| 6,069,168 | A | 5/2000 | Horrobin et al. |
| 6,162,801 | A | 12/2000 | Kita |
| 6,207,656 | B1 | 3/2001 | Carswell et al. |
| 6,296,861 | B1 | 10/2001 | Perricone .................... 424/401 |
| 6,299,896 | B1 | 10/2001 | Cooper et al. |
| 6,555,573 | B2 | 4/2003 | Rosenbloom |
| 6,592,896 | B2 | 7/2003 | Rosenbloom |
| 6,596,313 | B2 | 7/2003 | Rosenbloom |

FOREIGN PATENT DOCUMENTS

| | | |
|---|---|---|
| JP | 6 199 646 | 7/1994 |
| JP | 07324037 A | 12/1995 |
| JP | 11 139 959 | 5/1999 |
| KR | 19910008661 | 9/1993 |
| WO | WO 97/18817 | 5/1997 |
| WO | WO 9718817 * | 5/1997 |
| WO | 0000162 A1 | 6/1998 |
| WO | WO 01/17484 | 3/2001 |
| WO | 0137788 A1 | 5/2001 |

OTHER PUBLICATIONS

Reuters, *OncoLink—University of Pennsylvania Cancer Center*, "OncoLink Cancer News", "Burn Cream Reduces Skin Toxicity During Radiation Therapy for Breast Cancer", Sep. 22, 2000 2pgs.

"A Fact Sheet on the Health Effects from Ionizing Radiation", Office of Radiation & Indoor Air Radiation Protection Division, US Environmental Protection Agency, EPA 402-F-98-010, May 1998.

Joseph F. Weiss, "Pharmacologic Approaches to Protectionagainst Radiation-induced Lethality and Other Damage", *Public Health Reviews* 24(3-4):205-431 (1996) Abstract.

Ishige, et al., "Flavonoids protect neuronal cells from oxidative stress by three distinct mechanisms", *Fee Radic Biol Med 2001* Feb. 15;30 Abstract.

Wang, "The therapeutic potential of flavonoids", *Expert Opin Investig Drugs Sep. 2000;9(9)*: 2103-19 Abstract.

Klimenko et al., "The blood kinin system of person swith a history of 1st-degree acture radiation sickness", *Lik Sprava* May -Jun. 1994;(5-6:81-3 Abstract.

Wadsworth et al., "Effects of Ginko biloba extract (Egb 761) and quercetin on lipopolysaccharide-induced signaling pathways involved in the release of tumor necrosis factor-alpha", *Biochem Pharmacol* Oct. 1, 2001;62, Abstract.

Kapoor S., "Protection of radiation-induced protein damage by curcumin", *Biophys Chem* Aug. 30, 2001;92(1-2):119-26 Abstract.

Inano et al., "Potent preventive action of curcumin on radiation—induced initation of mammary tumorigenesis in rats", *Carcinogenesis* Oct. 2000;21(10): 1835-45 Abstract.

Sharma et al., "Sprice extracts as dose-modifying factors in radiationinactivation of bacteria", *J Agric Food Chem* Apr. 2000;48(4):1340-4 Abstract.

Strickland, "Immune regulation by polysaccharides: implications for skin cancer", J. Photochem Photobiol B Oct. 2001;63(1-3):132-40 Abstract.

Gessler, et al. "Radiation-protective effect of S-methylmethionine (vitamin U)", *Prikl Biokhim Mikrobiol* Nov.-Dec. 1996;32 (6):666-8 Abstract.

Nagler, et al., "Redox metal chelation ameliorates radiation-induced bone marrow toxicity in a mouse model", *Radiat Res* Aug. 2001; 156(2):205-9 Abstract.

Horyn et al., "The effect of sodium alpha-ketoglutarate on the indices of the peripheral blood and lipid peroxidation and on the enzyme activity of antioxidant protection in irradiated rats" *Fizol Zh* 2000;46(3):57-66.

Legeza, et al., "Prostaglandins—their role in the mechanisms of the development of the primary reaction to radiationsyndrome", *Radiats Biol Radioecol* Jan.-Feb. 1994;34(1):32-8.

Novozhenov, et al., "Changes in lipid peroxidation and the antioxidant system in patients with acute radiation sickness", *Voen Med Zh* Apr. 1993;(4):38-40, 80 Abstract.

Chaialo, et al., "Free-radical processes and blood antioxidant systems in the late period following acute radiation sickness", *Med Radiol (Mosk)* 1991;36(5):20-1 Abstract.

Bazhan, "Lipid peroxidation and the antioxidant system in subjects exposed to the influence of extreme factors", *Lik Sprava* Dec. 1998;(8):47-50 Abstract.

Beckman, et al., "Radiation therapy impairs endothelium-dependent vasodilation in humans", *J Am Coll Cardiol* Mar. 1, 2001;37(3):761 Abstract.

Castillo, et al., "Antiosidant activity and radioprotective effects against chromosomal damage induced in vivo by X-rays of flavan-3-ols (Procyanidins) from grape seeds (*Vitis vinifera*): comparative study versus other phenolic and organic compounds", *J Agric Food Chem* May 2000;48(5):1738-45 Abstract.

Weiss, et al., "Radioprotection by antioxidants", *Ann N Y Acad Sci* 2000;899:44-60 Abstract.

Weiss, "Pharmacologic approaches to protection against radiation-induced lethality and other damage", *Environ Health Perspect* Dec. 1997;105 Suppl6:1473-8 Abstract.

Baraboi, et al., "Mechanism of the antistressor and antiradiation action of plant phenol compounds", *Ukr Biokhim Zh* Nov.-Dec. 1998;70(6):13-23 Abstract.

Wu, et al., "Synthesis and bio-activity of coumarin derivatives and studies on its relationships between activity and lipophilicity", *Yao Xue Xue Bao* 1993;28(4):266-72 Abstract.

Thresiamma, et al., "Protective effect of curcumin, ellagic acid and bixin on radiation induced toxicity", *Indian J Exp Biol* Sep. 1996;34(9):845-7 Abstract.

Deneke, "Thiol-based antioxidants", *Curr Top Cell Regul* 2000;36:151-80 Abstract.

Il'iuchenok, et al., "Pharmacological and radioprotective properties of some gamma-pyrone derivatives (flavanones and flavanols)", *Farmakol Toksikol* Sep.-Oct. 1975;38(5):607-12.

Kapitanov, et al., "Radiation-protective effectiveness of lycopene", *Radiats Biol Radioecol* May-Jun. 1994;34 (3):439-45 Abstract.

Beliaev, et al., "Modification of the body's resistance to acute ionizing radiationby synthetic beta-carotene", *Vopr med Khim* Nov.-Dec. 1992;38(6):39-42 Abstract.

Chigareva, et al., "Radio-protective effect of sulfur-containing methylfuran derivatives and the role of thiols in its realization", *Radiobiologiia* Nov.-Dec. 1983;23(6):816-9 Abstract.

Samoilov, et al., "The radioprotective and antioxidant properties of solubilized alpha-tocopheraol acetate", *Eksp Klin Farmakol* Jul.-Aug. 1992;55(4):42-4 Abstract.

Kamat, et al., "Chlorophyllin as an effective antioxidant against membrane damage in vitor and ex vivo", *Biochim Biophys Acta* Sep. 27, 2000;1487(2-3):113-27 Abstract.

Uma, et al., "Radiation protection by the ocimum flavonoids orientin and vicenin: mechanisms of action", *Radiat Res* Oct. 2000;154(4):455-60 Abstract.

Moskalenko, et al., "The role of immunological mechanisms in the development of the late sequelae of nuclear disasters", *Lik Sprava* Jun. 1999;(4):3-8 Abstract.

Ovsiannikova, et al., "Efficacy of antioxidant preparations used for correction of impairment of oxidative homeostasis in Chernobyl liquidators", Radiats Biol Radioecol Mar.-Jun.;39(2-3):318-21, Abstract.

Afanas' et al., "chelating and free radical scavenging mechanisms of inhibitory action of rutin and quercetin in lipid peroxidation", *Biochem Pharmacol* Jun. 1, 1989;38(11):1763-9 Abstract.

Ishige, et al., "Flavonoids protect neuronal cells from oxidative stress by three distinct mechanisms", *Free Radic Biol Med* Feb. 15, 2001;30(4):433-46 Abstract.

Shobana, et al., "Antioxidant activity of selected Indian spices", *Prostaglandins leukot Essent Fatty Acids* Feb. 2000;62(2):107-10 Abstract.

Tiukavkina, et al., "Dihydorquercetin—anew antioxidant and biologically active food additive", Vopr Pitan 1997;(6):12-5 Abstract.

Plumb, et al., "Antioxidant properties of flavonal glycosides from tea", *Redox Rep* 1999;4(1-2):13-6 Abstract.

Skaper, et al., "Quercetin protects cutaneous tissue-associated cell types including sensory neurons from oxidative stress induced by glutathione depletion: cooperative effects of ascorbic acid", *Free Radic biol med* 1997;22(4):669-78 Abstract.

Jones, et al., "Radioprotective effect of free radical scavenging enzymes", *J Otolaryngol* Oct. 1990;19(5):299-306 Abstract.

Boloor, et al., "Chlorophyllin as a protector of mitochondrial membranes against gamma-radiation and photosensitization", *Toxicology* Nov. 30, 2000;155(1-3):63-71 Abstract.

Kim, et al, "In vivo radioprotective activity of Panax ginseng and diethyldithiocarbamate", In Vivo Sep.-Oct. 1993;7(5):467-70 Abstract.

Rice-Evans,et al., "The relative antioxidant activities of plant-derived *polyphenolic* flavonoids", Free *Radic Res* 22:4:375-83 1995 Summary.

Gillis, "Panax ginseng pharmacology: a nitric oxide link", *Biochemical Pharmacology* 54:1-8 (1997) Summary.

Robak, et al., "Bioactivity of flavonoids", *Pol J Pharmacol* Nov.-Dec. 1996;48(6):555-64 Abstract.

Bursel, et al., "Can protein kinase C inhibition and vitamin E prevent the development of diabetic vascular complications?", *Diabetes Res Clin Pract* Sep. 1999;45 (2-3):169-82 Abstract.

Freedman, et al., "Select flavonoids and whole juice from purple grapes inhibit platelet functionand enhance nitric oxide release", *circulation* Jun. 12, 2001;103(23):2792-8 Abstract.

Lin, et al., "Recent studies on the biofunctions and biotransformations of curcumin", *Biofactors* 2000;13(1-4):158-8 Abstract.

Isoherranen, et al., "Ultraviolet irradiation induces cyclooxygenase-2 expression in keratinocytes", *Br J Dermatol* Jun. 1999;140(6):1017-22 Abstract.

Duarte, et al., "Vasodilator effects of quercetin in isolated rat vascular smooth muscle", *Eur J Pharmacol* Aug. 1993 239:1-7 Abstract.

Giugliano, et al., "Oxidative stress and diabetic vascular complications", *Diabetes Care* Mar. 1996;19(3):257-67 Abstract.

On, et al., "Vitamin c prevents radiation-induced endothelium-dependent vasomotor dysfunction and de-endothelialization by inhibiting oxidative damage in the rat", *Clin Exp* Pharmacol Physiol Oct. 2001;28(10):816-21 Abstract.

Konopacka, et al., "Modifying effect of vitamins C, E and beta-carotene agaist gamma-ray-induced DNA damage in mouse cells", *Mutat Res* Sep. 11, 1998;417(203):85-94 Abstract.

Shope, "Radiation-induced skin injuries from fluoroscopy", Scientific Exhibit 060PH at the 81st Scientific Assembly and Annual Meting of the Radiological Society of North America, Nov. 26-Dec. 1, 1995, Radiology vol 197(P) Supplement, P449 Abstract.

Noble-Adams, "Radiation-induced skin reactions. 2: Development of a measurement tool", Br J Nurs Oct. 14-27, 1999;8(18):1208-11 Abstract.

Noble-Adams, "Radiation-induced skin reactions. 3: Evaluating in RISRAS", *Br J Nurs* Oct. 28-Nov. 10, 1999;8(19):1305-12 Abstract.

Cusma, et al., "Real-time measurement of radiation exposure to patients during diagnostic coronary angiography and percutaneous interventional procedures", *J Am coll Cardiol* Feb. 1999;33(2):427-35 Abstract.

Newall et al., "The control of oral secretions in bulbar ALS/MND", *J. Neurol Sci*, Aug. 1996 vol. 139 Supp;:43-44.

Morgan et al., "Topical treatment of radiation induced dermatitis with N-acetylcysteine (NAC)(Meeting Abstract)", *Proc Annu Meet Am Assoc Cancer Res.* 1996; 37:A4142.

William F. dial, Cosmetic Dermatology, "Topical Vitamin C May Help Protect Skin From UV Damage", Dec. 1991, pp. 34-35.

Bernard Idson, College of Pharmacy, University of Texas at Austin, Ultraviolet Irradiation Injury and Repair, Jan. 1992, pp. 22-24 and pp. 81-81.

Bissett et al., "J. Soc. Cosmet. Chem., "Protective effect of a topically applied anti-oxidant plus an anti-inflammary agent against ultraviolet radiation-induced chronic skindamage in the hairless mouse, 43, Mar./Apr. 1992, pp. 85-92.

Darr et al., "*British Journal of Dermatology*,"Topical vitamin C protects porcine skin from ultraviolet radiation-induced damage (1992) 127, 247-253.

*Dermatology Times*, "New Aqueous Vitamin C blocks UV rays"1991.

Fuchs et al., "Acute Effects of Near Ultraviolet and Visible Light on the cutaneous Antioxidant Defense System"Oct. 3, 1988, pp. 739-744.

vitamin E (Tocopherol) vs. Vitamin E Acetate, Roche, Jun. 1991.

Schmuth, et al., "Permeability barrier function of skin exposed to ionizzing radiation" Arch Dermatol Aug. 2001; 137(8):1019-23.

Katiyar, et al., "Green tea polyphenol (-)-epigallocatechin-3-gallate treatment of human skin inhibits ultraviolet radiation-induced oxidative stress" Carcinogenesis Feb. 2001;22(2):287-94.

Walker RI, "Requirements Of Radioprotectors For Military and Emergency Needs", PubMed Abstract, Pharmacol Ther. 1988;39(1-3):13-20.

Weiss et al., Protection Against Ionizing Radiation by Antioxidant Nutrients And Phytochemicals, PubMed Abstract, Toxicology. Jul. 15, 2003;189(1-2):1-20.

Packer, et al, "Alpha-Lipoic Acid As A Biological Antioxidant", Free Radical Biology & Medicine, vol. 19, No. 2, pp. 227-247, 1995.

Kumar, et al, Nutritional Approaches to Radioprotection: Vitamin E, PubMed Abstract, Mil Med. Feb. 2002;167 (2 Suppl):57-9.

Weiss et al., "Radioprotection By Antioxidants", PubMed Abstract, Ann NY Acad Sci. 2000;899:44-60.

Petryna, Effect Of Gamma-Radiation On The Content Of Vitamin E In Rats, PubMed Abstract, Ukr Biokhim Zh. May-Jun. 2002;74(3):104-8.

Boloor et al., Chlorophyllin As A Protector Of Mitochondrial Membranes Against Gamma-Radiation And Photosensitization, PubMed Abstract, Toxicology. Nov. 30, 2000;155(1-3):63-71.

Kamat et al, Chlorophyllin As An Effective Antioxidant Against Membrane Damage In Vitro and Ex Vivo, PubMed Abstract, Biochim Biophys Acta. Sep. 27, 2000;1487(2-3):113-27.

Kumar, et al, Scavenging Of Reactive Oxygen Species By Chlorophyllin: An ESR Study, PubMed Abstract, Free Radic Res. Nov. 2001;35(5):563-74.

Devasagayam et al., Prevention of Singlet Oxygen-Induced DNA Damage By Lipoate, PubMed Abstract, Chem Biol Interact. Jan. 1993;86(1):79-92.

Riley, "Free Radicals In Biology: Oxidative Stress and The Effects Of Ionizing Radiation", PubMed Abstract, Int J Radiat Biol. Jan. 1994;65(1):27-33.

Brach, et al, Ionizing Raditation Induces Expression And Binding Activity of The Nuclear Factor Kappa B, PubMedAbstract, J Clin Invest. Aug. 1991;88(2):691-5.

Prasad et al, Activation Of Nuclear Factor Kappa B In Human Lymphoblastoid Cells By Low-Dose Ionizing Radiation, PubMed Abstract, Radiat Res. Jun. 1994;138(3):367-72.

Zhou, et al., A High Dose Of ionizing Radiation Induces Tissue-Specific Activation Of Nuclear Factor-kappaB In vivo, PubMed Abstract, Radiat Res. Jun. 1999;151(6):703-9.

Morales-Ramirez et al., Effect Of Chlorophyllin On Gamma Ray Induced Micronuclei In Polychromatic Erythrocytes Of Murine Peripheral Blood Determined By The ABC Strategy, PubMed Abstract, Mutat Res Feb. 1996;367(2):51-6.

Biewenga et al., "The Pharmacology Of The Antioxidant Lipoic Acid", PubMed Abstract, Gen Pharmacol. Sep. 1997;29(3):315-31.

Sokoloski et al., Induction Of the Differentiation Of HL-60 Promyelocytic leukemia Cells By vitamin E and Other Antioxidants In Combination With Low Levels Of V itamin D3: Possibe Relationship To NF-KappaB, PubMed Abstract, Leukemia. Sep. 1997;11(9):1546-53.

Zimmer, et al., Influence of Alpha-Lipoic Acid On Intracellular Glutathione In Vitro And In Vivo; 42:829-31 (1992).

Packer, Alpha-Lipoic Acid: A Metabolic Antioxidant Which Regulates NF-Kappa B Signal Transduction And Protects Against Oxidative Injury, PubMed Abstract, Drug Metal Rev. May 1998;30(2):245-75.

Packer, Alpha-Lipoic Acid, 30:2:245-275 (1998).

Scott, et al., Lipoic And Dihydrolipoic Acids As Antioxidants. A Critical Evaluation: 20:2:1 19-33 (1994).

Suzuki et al, Antioxidant Activities Of Dihydrolipoic Acid And Its Structural Homologues: 18:2:115-22 (1933).

Suzuki et al., Alpha-Lipoic Acid Is A Potent Inhibitor of NF-Kappa B Activation In Human T Cells: 189:1709-15 (1992).

Iwata et al., Differential Regulation Of Vitamin D Receptors In Clonal Populations Of A Chronic Myelogenous Leukemia Cell Line, Exp. Cell Res. May 25, 1996;225(1):143-50.

Radhika et al., Induction Of Differentiation In Murine Erythroleukemia Cels By 1 Alpha,25-Dihydorxy Vitamin D3, Cancer Lett. Apr. 14, 1995;90(2):225-30.

Abraham et al., Role of Chlorophyllin As An In Vivo Anticlastogen: Protection Against Gamma-Radiation And Chemical Clastogens, PubMed Abstract, Mutat Res 1994 Sep.:322(3):209-12.

Elliott Middleton, Jr., Chithan Kandaswami and Theoharis C. Theoharides, *The effects of Plant Flavnoids on Mammalian Cells: Implications for Inflammation, Heart Disease and Cancer*, vol. 52, Issue 4, 673-751, Dec. 2000.

Graham M. M., et al., "Pharmacological Alteration Of The Lung Vascular Response To Radation", International Journal of Radiation Oncology, Biology, Physics (1990), vol. 19, No. 2, pp. 329-339.

Starikovich, L.S., et al., "Effect of a Vitamin D3-Based Nutritional Supplement ("Videchol") on Carbohydrate metabolism of Rats Following Chronic Low Dose-Rate Irradiation", J. Radiol. Rot. (Sep. 2001), vol. 21, No. 3, pp. 269-276.

Hanada K., et al. "Protective Effect of 1a, 25-Dihydroxyvitamin V3 Against UVB injury-Possible role of the Vitamin D3-induced metallothionein", Int. Congr. Ser., (1993), vol. 1021, pp. 479-482.

Sho, K., et al., "Change of Nitroxide Radical Reduction in Mouse Lung After Irradiation: Analysis Using L-band electron Spin Resonance (ESP)", Journal of Shiga Medical University, vol. 12, 1997, pp. 17-24 (Abstract Only).

Kennedy, M., et al., "Successful and Sustained Treatment of Chronic Radiation Proctitis With Antioxidant Vitamins E and C", the American Journal of Gastroenterology, (Apr. 2002), vol. 96, No. 4, pp. 1080-1084.

Shaheen A., et al. "Role of vitamin A in Modulating the Radiation-induced Changes in Intestinal Disaccharidases of Rats Exposed to Multifractionated Gamma-radiations" Strahlentherapie und Onkologie, (1994), vol. 107, No. 8, pp. 467-470.

Wang, Deqing et al., "Experimental Study of Anti-radiation effectiveness of Astragalus Total Flavonoids", Zhonghua Fangshe Yixue Yu Fanghu Zazhi, (1996), vol. 16, No. 6, pp. 399-401 (Abstract Only)

Roche, Certificate of Analysis for D-Panthenol, by C. Conduit, Nov. 10, 1999.

Roche, Certificate of Analysis for di-Alpha Tocopheryl Acetate, by Karen Moll, Mar. 3, 2000.

Roche, Certificate of Analysis for vitaminA Palmitate, by Dr. R. Schwetzler, May 2, 2000

Roche, Certificate of Analysis for Ascorbyl Palmitate, by Dr. K. Deutschman, Nov. 12, 1999.

Henahan J., *Dermatology Times*, "New Aqueous Vitamin C blocks UV rays" 1991.

American Academy of Dermatology, "Eczema/Atopic Dermatitis", 1999, pp. 1-4, retrieved Oct. 15, 2002 @ http://www.aad.org/pamphlets/eczema.html.

Ponec M., et al., "The formation of competent barrier lipids in reconstructed hman epidermis requires the presence of vitamin C", *J Invest Dermatol*, Sep. 1997; 109(3): 348 55.

Foster, James, "Sunburn", *eMedicine Journal*, Aug. 21, 2001, vol. 2, No. 8, downloaded Jun. 17, 2002, pp. 1-12 at http://www.emedicine.com/EMERG/topic798.htm.

Achre Report, "What is Ionizing Radition?", retrieved Mar. 1, 2002, download @ http://tis.eh.doe.gov/ohre/roadmap/achre/intro_9_1.html.

Shuk-mei, H., "Drug Screening Methods for Estorgen Receptor Beta (Erb) Modulators", *BioScience Valuation*, Pharmalicensing, Mar. 8, 2002, download retrieved mar. 8, 2002 @ http://atlas.pharmalicensing.com/licensing/displicopp/548.

Hyatt, B.A., et al., "The roles of FGF's, BMP4, and SHH in Transdifferentiaion of Mouse Tracheal Epithelium in Mesenchyme-free Culture", Children's Hospital Medical Center, Cincinnati, Developmental Biology Annual Meeting, Jul. 2001, Reprinted by Cepheid, pp. 1-4.

Mirasolo, S., "Actinic Dermatitis (Sunburn)", Sports Medicine Articles, Northeast Rehab Health Network, retrieved Jan. 10, 2002 @ http://www.rehabnet.com/Sports/Actinic%20Dermatitis.htm pp. 1-2.

Himmerich S., et al., "Effect of Vitamins E and C on Nitric Oxide Production in Oxidized Low Density Lipoprotein Treated Human Aortic Endothelial Cells", *Academic Press*; 2000, internet download at http://www.academicpr3ess.com/www/journal/niox/9204.html.

Asahi K, et al., "Nitric Oxide Inhibits the Formation of Advanced Glycation End Products", *Kidney Int* Oct. 2000;58(4):1780-7.

Van Acker et al., "Structural Aspects of Antioxidant Activity of Flavonoids", *Free Radic Biol Med* 1996;20(3):331-42.

Roche Vitamins for Cosmetics, pp. 1 to 5, Sep. 4, 1985.

"Ultraviolet Irradiation Injury and Repair" by Bernard Idson, Ph.D., Jan. 1992, pp. 78 to 81.

"Role of Nitric Oxide in Pain" by Jai pal Singh, doo Hyam Lee, Asavari Wagle and David Lodge, 2000 Academic Press.

"The Neuronal NO synthase inhibitor 7-nitro-indazole facilitates the antinociception elicited by the electrical stimulation of the secondary somatosensory cortex in the rat" by Ryotaro Kuroda, Atsufumi Kawabata, Naoyuki Kawao, Wakana Umeda, Hiroko Yoshmura, 2000 Academic Press.

"Over-the Counter Drug is Treatment for Alzheimer's" by Terri Mitchell and Amber Needham, LE Magazine, Nov. 2000, p. 1 to 9.

"Ascorbate 6-palmitate protects human erythrocytes from oxidative damage", Jan. 1999, PubMed.

"Analgesic activity of certain flavone derivatives: a structure-activity study", Jan. 1993, PubMed.

Medscape Medline Abstract, "The hydroxyl free radical reactions of ascorbyl palmitate as measured in various in vitro models" by Perricone N, Nagy K, Horvath F, Dajko G, Uray I, Zs.-Nagy I, Sep. 1999.

Medscape Medline Abstract, "Making vitamin C lipophilic enhances its protective effect against free radical induced peroxidation of low density lipoprotein" by Liu ZQ, Ma LP, Liu ZL, Sep. 1998.

Medscape Medline Abstract, "Novel pharmacological activity of a vitamin (novel) pharmacological action of vitamin D)", by Fukuoka M, Ohta T and Kiyoki M, Oct. 1997.

Medscape medline Abstract, "A vitamin D(3) derivative (CB1093) induces nerve growth factor and presents neurotrophic deficits in streptozotocin-diabetic rats", by Riaz S, malcangio M, Tomlinson DR, Nov. 1999.

Ramakrishnan et al., Radioprotection of hematopoietic tissues in mice by lipoic acid, PubMed, PMID: 1594763, Radiat. Res., Jun. 1992;130(3):360-5, Abstract.

Munker et al., "A new series of vitamin D analogs is highly active for clonal inhibition, differentiation, and induction of WAF1 in myeloid leukemia", PubMed, PMID: 8822940, Blood. Sep. 15, 1996;88(6):2201-9, Abstract.

Jung et al., "1,25 (OH)2-16ene-vitamin D3 is a potent antileukemic agent with low potential to cause hypercalcemia", PubMed, PMID: 8207963, Leuk. Res. 1994 Jun.;18(6):453-63, Abstract.

Panah et al., DiscoveRx, , "Homogeneous Assays for Tyrosine Kinase and /tyrosine Phosphatase Activity Using β-Galactosidase Enzyme Fragment Complementation", DiscoveRx Corporation, Fremont, CA, Abstract, No publication date available.

Li et al., [Regulative function of extracelluar regulated protein kinases and telomerase in apoptosis of hepatocrcinomatous and leukemic cell SMMC-7721], PubMed, PMID:12223143, Zhonghua Gan Zang Bing Za Zhi Aug. 2002;10(4):287-8, Abstract.

Coles, S., "Quercetin: A Review of Clinical Applications", Natural Mmedicine Online, Jul. 2000.

Williams, D., Dave's "Psoriasis Info—Nature's Rain Moisturizers," 1999, World Wide Web.

Williams, DG, Quercetin, "Protect your Health With This Important Flavonoid", ImmuneSupport.com., Apr. 1, 1994.

Healthnotes, Inc., "Quercetin," 1999, World Wide Web, pp. 1-3.

Riley, PA, "Free Radicals In Biology: Oxidative Stress And The Effects Of Ionizing Radiation," *Int. J. Radiat Biol.* Jan. 1994; 65(1):27-33 (Abstract Only).

* cited by examiner

ORAL COMPOSITIONS AND METHODS FOR PREVENTION, REDUCTION AND TREATMENT OF RADIATION INJURY

CROSS-REFERENCE TO RELATED APPLICATIONS

This application is a continuation-in-part of U.S. application Ser. No. 09/993,003 filed on Nov. 6, 2001, which is currently pending.

BACKGROUND OF THE INVENTION

1. Field of the Invention

The present invention relates to oral compositions and methods for preventing, reducing and treating radiation injury.

2. Description of the Prior Art

It is generally known that extensive radiation exposure or exposure to strong radiation may cause radiation injury. Radiation injury may range from less serious injuries such as radiation dermatitis to more serious injuries such as those causing vomiting, bone marrow failure and intestinal death. Such injuries or damage may be caused by radiation emitted from x-rays such as those used in diagnostic equipment, γ-rays such as those emitted from radioactive materials or from numerous other sources.

Many attempts have been made to reduce, control or cure radiation injury. U.S. Pat. No. 5,543,140 to Nakai et al discloses a method of preventing or inhibiting radiation injury by administering interleukin-1-α derivatives. In particular, Nakai et al uses an interleukin-1-α modified by replacing the Asn at the 36 position with Asp, and replacing the Cys at the 141 position with Ser. The modified interleukin-1-α derivative is preferably produced using recombinant DNA techniques, which are complicated and burdensome. In addition, the potential adverse side effects of the modified Interleukin-1-α derivatives are not well known.

U.S. Pat. No. 5,767,092 to Koezuka et al. discloses a composition, which may be therapeutically or prophylactically useful in promoting bone marrow cell proliferation and protecting human bone marrow cells against radiation damage. The composition disclosed in Koezuka et al. contains α-galactosylceramide. However, radiation may cause other injuries in addition to damage to bone marrow cells and thus this composition has limited applicability.

There still remains a need in the art for effective compositions and methods to prevent, reduce and treat radiation injury.

Accordingly, it is an objective of certain embodiments of the present invention to provide an oral composition that, when ingested, will prevent, reduce or treat radiation injury.

It is further objective of certain embodiments of the present invention to provide methods to effectively prevent, reduce or treat radiation injury by oral administration of a composition that, when ingested, will prevent, reduce or treat radiation injury.

It is a still further objective of certain embodiments of the present invention to provide methods of administering a composition to prevent, reduce or treat radiation injury using a combination of oral and topical administration.

These and other objects of the present invention will be apparent from the summary and detailed descriptions of the invention, which follow.

SUMMARY OF THE INVENTION

In a first aspect, the present invention relates to an oral composition for preventing, reducing or treating radiation injury. The oral composition includes a compound that regulates cell differentiation and/or cell proliferation, an antioxidant and at least one of a pharmaceutically acceptable carrier for an oral composition or at least one other ingredient useful in the prevention, reduction or treatment of radiation injury.

In a second aspect, the present invention relates to a method of orally administering a composition for the prevention, reduction or treatment of radiation injury. In the method, an effective amount of a suitable composition is orally administered to a person at risk for radiation exposure or to a person who has already been exposed to radiation to prevent, reduce or treat radiation injury.

DETAILED DESCRIPTION OF THE PREFERRED EMBODIMENTS

In a first aspect, the present invention relates to an oral composition for the prevention, reduction or treatment of radiation injury. In this aspect of the invention, the oral composition includes a mixture of a compound that regulates cell differentiation and/or cell proliferation, an antioxidant and a pharmaceutically acceptable carrier for an oral composition.

Radiation injury may include injury or damage to any part of the human body caused by exposure to radiation. Such injury or damage may include radiation dermatitis, bone marrow cell damage, intestinal damage, and symptoms or conditions such as cancer, and DNA mutation that may be caused either directly or indirectly, by radiation exposure. However, radiation injury as it is used in this application does not include sunburn. The compositions and methods of the present invention may be employed to treat radiation injury resulting from exposure to one or more of proton radiation, fluoroscopic radiation, ultraviolet radiation, alpha radiation, beta radiation and gamma radiation. The invention is particularly useful for persons who are, or will be, engaging in activities involving high risk of radiation exposure. Also, the invention can be employed to treat persons exposed to radiation as a result of a radiation attack, a nuclear accident, radiation from diagnostic instruments and therapeutic radiation used to treat, for example, cancer. In a preferred embodiment, the various compositions and methods of the present invention are employed to prevent, reduce or treat damage resulting from exposure to non-therapeutic radiation from sources such as diagnostic instruments, radiation attack, a nuclear accident, the performance nuclear medicine on others, prolonged exposure to the sun, etc.

The radiation injury prevented or treated by the compositions and methods of the present invention may be caused by exposure to non-therapeutic radiation, such as, for example, accidental radiation exposure, exposure to radioactive materials released by terrorists or nuclear accidents, and exposure to diagnostic instruments such as an x-ray machine, a CT-scan, or a synchrotron, all of which employ radiation. Alternatively, the radiation injury prevented or treated by the compositions and methods of the present invention may be caused by exposure to therapeutic radiation, such as radiation therapy used in cancer treatment. Preferably, the radiation injury being prevented, reduced or treated in the present invention is of the type caused by non-therapeutic radiation.

The compound that regulates cell differentiation and/or cell proliferation that may be used in the composition of the present invention may be selected from suitable compounds that have this activity. Suitable compounds that regulate cell differentiation and/or cell proliferation are those that do not induce significant, adverse side effects when administered to a patient in amounts that regulate cell differentiation and/or cell proliferation, and which do not react with one or more of the ingredients of the composition resulting in a substantial loss of activity of one or more of the ingredients. Preferred compounds for regulating cell differentiation and/or cell proliferation are those that occur naturally in the human body and/or materials obtained from plants or animals which may be administered to humans without significant, adverse side effects in the amounts used, or derivatives thereof.

More preferably, the compounds that regulate cell differentiation and/or cell proliferation used in the present invention inhibit or prevent cell differentiation or cell proliferation. Even more preferably, the compounds that regulate cell differentiation and/or cell proliferation used in the present invention accomplish at least one of the following: maintenance of cellular homeostasis and normal cell metabolism, regulation of cell differentiation, induce certain cancer cells to differentiate into normal cells, preferably by working in combination with vitamin A, maintenance of the epidermal permeability barrier, inhibition of cancer cell differentiation, and inhibition of cancer cell proliferation.

Exemplary compounds that regulate cell differentiation and/or cell proliferation are vitamin $D_3$, vitamin $D_3$ analogs, compounds that may be converted or metabolized into vitamin $D_3$ in the human body, and metabolites thereof Exemplary compounds that may be converted or metabolized into vitamin $D_3$ include common cholesterols illustrated below. The cholesterol illustrated below may be converted into Provitamin D when a hydrogen is removed from the number 7 carbon, which then forms a double bond with the number 8 carbon, in the second, or 'B' ring of the cholesterol molecule. The cholesterol is 'oxidized' (that is, an electron is removed with the hydrogen atom), so that the double bond is a consequence of 2 mutually shared electrons between carbons 7 and 8.

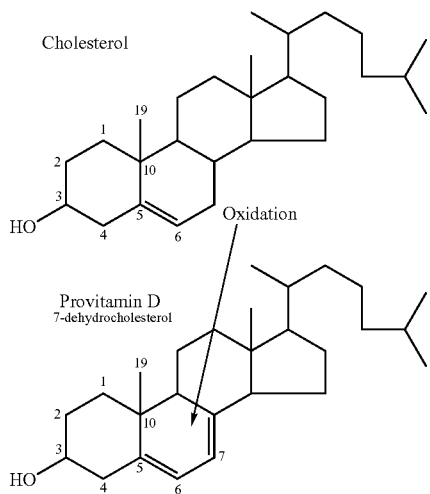

Provitamin D may be converted to Vitamin $D_3$ by the action of ultraviolet light through human skin. In this reaction, the B ring of the sterol molecule is opened.

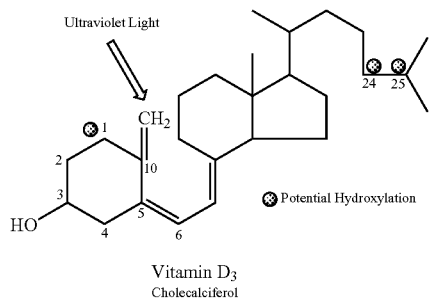

Vitamin $D_3$
Cholecalciferol

Cholecalciferol, which is Vitamin $D_3$, may be further converted into another vitamin D intermediate, 25-hydroxycholecalciferol, in the liver by mitochondrial hydroxylase, in the presence of NADPH, and molecular oxygen.

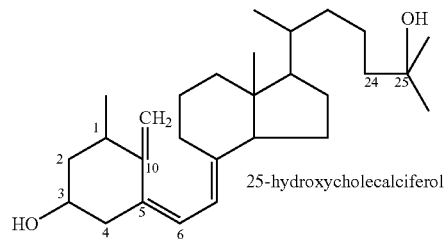

When more active vitamin $D_3$ is required, 25-hydroxycholecalciferol is transported to the kidney where a new hydrolase enzyme is synthesized. This enzyme introduces another hydroxyl group at position 1, and the bioactive form of Vitamin $D_3$, calcitriol, is produced.

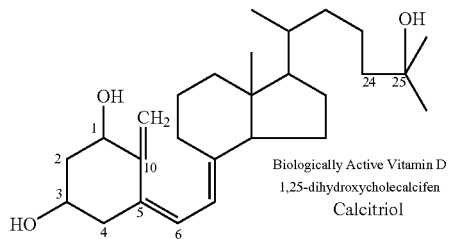

Exemplary vitamin $D_3$ analogs include 1(S), 3(R)-dihydroxy-20(R)-(1-ethoxy-5-ethyl-5-hydroxy-2-heptyn-1-yl)-9,10-seco-pregna-5(Z), 7(E), 10 (19)-triene. Exemplary vitamin $D_3$ metabolites include 1, 25-dihydroxyvitamin $D_3$. Also, pharmaceutically acceptable salts of the compounds that regulate cell differentiation and/or cell proliferation may be employed. The most preferred compound that regulates cell differentiation and/or cell proliferation is vitamin $D_3$.

The compound that regulates cell differentiation and/or cell proliferation is used in an amount effective to regulate cell differentiation and/or cell proliferation when orally administered to a patient in the oral composition of the present invention.

Another ingredient in the oral composition of the present invention is the antioxidant. The antioxidant may be a single compound or material or a mixture of two or more compounds and/or materials. Compounds and materials which may be used as antioxidants are those which exhibit antioxidant activity when administered to a patient without causing any severe adverse side affects when used in an amount effective to provide sufficient antioxidant activity, and which do not react with one or more of the ingredients of the composition resulting in a substantial loss of activity of one or more of the ingredients. Preferred antioxidants are those that occur naturally in the human body and/or materials obtained from plants or animals, or derivatives thereof.

Preferred antioxidants are selected from ascorbic acid (vitamin C) and its esters, for example, ascorbyl palmitate; vitamin A and its esters, for example, vitamin A palmitate; vitamin E and its esters, for example, vitamin E acetate; α-lipoic acid, especially DL-α-lipoic acid; carotenoids such as β-carotene; chlorophyllin and its salts; coenzyme Q10; glutathione; green tea polyphenols, such as (−)-epigallocatechin-3-gallate; catechin; galangin; rutin; luteolin; morin; fisetin; silymarin; apigenin; gingkolides; hesperitin; cyaniding; citrin; curcuminoids and structurally similar derivatives thereof which exhibit antioxidant activity. Even more preferably, mixtures of two or more antioxidants are employed in the composition of the present invention. Particularly preferred antioxidant mixtures are ascorbyl palmitate with one or more of vitamin A, vitamin E acetate and α-lipoic acid especially DL-α-lipoic acid. The antioxidants may also be used in the form of their pharmaceutically acceptable salts and this may be preferred in some cases to increase solubility or dispersability, to reduce adverse side effects, etc.

Structurally similar derivatives of one or more of these compounds, which exhibit antioxidant activity when administered in the oral compositions of the present invention, may also be employed. By "structurally similar derivatives" is meant derivatives that exhibit antioxidant activity and contain at least one significant, common structural element with the compound or material from which it is derived.

In another preferred embodiment, the antioxidant used in the composition of the present invention may include one or more antioxidant enzymes. The antioxidant enzymes useful in the present invention are those capable of scavenging radicals, promoting radical scavengers or preventing radical formation. The preferred antioxidant enzymes useful in the present invention include superoxide dismutase, catalase, glutathione peroxidase and methionine reductase. Other antioxidant enzymes with activities similar to those mentioned explicitly above, may also be used. In addition, one or more of the antioxidant enzymes may act in combination with one or more of the antioxidant compounds in the composition to, for example, scavenge free radicals and/or prevent cell damage in the skin.

The antioxidant component of the composition is used in an amount effective to provide significant antioxidant activity when administered to a patient in the composition of the present invention.

The ratio of the amount of the compound that regulates cell differentiation and/or cell proliferation to the amount of antioxidant employed in the compositions of the present invention is from about 200 IU per gram of antioxidant to about 3 million IU per gram of antioxidant. More preferably, the ratio of the amount of the compound that regulates cell differentiation and/or cell proliferation to the amount of antioxidant employed in the compositions of the present invention is from about 1800 IU per gram of antioxidant to about 1 million IU per gram of antioxidant, and, most preferably the ratio is from about 5000 IU per gram of antioxidant to about 200,000 IU per gram of antioxidant.

The antioxidants used in the composition of the present invention are preferably selected not only for their antioxidant activity, but also based on other beneficial effects that particular compounds may provide. For example, a racemic mixture of α-lipoic acid not only has a strong antioxidant activity but also has a recycling effect on vitamins C and E, and thus is a particularly preferred antioxidant for the present invention. In addition, α-lipoic acid can function in both lipid and non-lipid environments. Similarly, vitamin E and its esters may contribute to an anti-cancer effect and may have beneficial effects on the skin and is thus is also a preferred antioxidant. Vitamin C and its esters are not only antioxidants, but also exhibit a strong combinatorial effect with vitamin E and its esters when used together. In fact, vitamin E and its esters, and vitamin C and its esters can mutually reinforce one another by a mechanism in which one antioxidant (reducing agent) acts as a regenerator for the oxidized form of the other.

Vitamin A (retinol or retinyl ester) may also have anti-cancer effects. In addition, vitamin A may also enhance the physiological mechanism of cell differentiation, inhibit malignant transformation, suppress tumor promotion and directly act against neoplastic cells. Vitamin A is also a fat-soluble material and thus is preferred for use due to this additional beneficial property. Preferably, vitamin A may be used in its ester forms, such as vitamin A palmitate, because the ester forms of vitamin A may be less irritating to the stomach.

Another particularly preferred antioxidant is green tea polyphenol or green tea extract, which contains compounds such as (−)-epigallocatechin-3-gallate, (−)-epigallocatechin-3-gallate, (−)-epigallocatechin and/or (−)-epicatechin. Studies (see Elmets, C. A. et al, J. Am. Acad. Dermatol., 44 (3); 425-32, March, 2001) have shown that green tea polyphenol or extract is effective in inhibiting erythema and preventing Langerjans cells from some forms of ultraviolet radiation damage.

Carotenoids such as β-carotene may also be included in the composition of the present invention as a preferred antioxidant. Several carotenoids have shown beneficial effects for the present application, such as enhancement of immune response, inhibition of mutagenesis and/or reduction of induced nuclear damage. Carotenoids can also protect against photo-induced tissue damage. Some carotenoids, including β-carotene, quench highly reactive singlet oxygen under certain conditions and can block free radical-mediated reactions.

Preferably, the antioxidant used in the composition of the present invention may also include one or more curcuminoids. Exemplary curcuminoids include curcumin (diferuloylmethane), desmethoxycurcumin (hydroxycirmamoyl feruloylmethane), and/or bis-desmethoxycurcumin (dihydroxydicinnamoyl methane) (see Drug Analysis by Chromatography and Microscopy, p. 169, Ann Arbor Science Inc., 1973), which may be purchased from commercial sources or isolated from turmeric. Methods for isolating curcuminoids from turmeric are known, (see Janaki and Bose, An Improved Method for the Isolation of Curcumin From Turmeric, J. Indian Chem. Soc. 44:985 (1967)). Alternatively, curcuminoids for use in the present invention can be prepared by synthetic methods. Curcumin not only has antioxidant properties but also may have anti-inflammatory, anti-tumor and other valuable properties.

Preferably, the antioxidant used in the composition of the present invention may also include chlorophyllin and/or its salts, because chlorophyllin and its salts may exhibit beneficial effects such as an anti-cancer effect, protection of DNA against ionizing radiation and other chemical mutagens, and fighting bad breath, nausea and indigestion, in addition to being a potent antioxidant. Chlorophyllin and its salts may be included in the composition of the present invention as part of the antioxidant. More preferably, chlorophyllin and its salts may be included in the composition of the present invention in amounts, which, when administered to a patient according to a method of the present invention, provide a daily dosage between about 20 milligrams and about 500 milligrams. Chlorophyllin and its salts may be an alfalfa extract or extracted from silkworm feces. Chlorophyllin and its salts may also be purchased from common commercial sources such as Aldrich Chemical Company.

Even more preferably, the antioxidant used in the composition of the present invention includes a combination of effective amounts of vitamin A or its esters, vitamin C or its esters, vitamin E and α-lipoic acid to achieve the beneficial effect of recycling vitamin C or its esters and vitamin E by α-lipoic acid.

Preferably, the composition of the present invention further includes one or more flavonoids and/or flavonoid derivatives. These flavanoids and/or flavanoid derivatives may have radioprotective effects. In addition, flavonoids and/or flavonoid derivatives such as quercetin may have other beneficial effects such as acting as an anti-inflammatory and maintaining the structural integrity of ischemic or hypoxic tissue, which may occur after radiation exposure. Exemplary flavonoids and flavonoid derivatives include 1,2,3,6-tetra-o-gallyol-β-d-glucose; 2'o-acetylacetoside; 3,3',4-tri-o-methyl-ellagic acid; 6,3',4'-trihydroxy-5,7,8-trimethoxyflavone; 6-hydroxy-luteolin; 6-hydroxykaempferol-3,6-dimethyl ether; 7-o-acetyl-8-epi-loganic acid; acacetin; acetoside; acetyl trisulfate quercetin; amentoflavone; apigenin; apiin; astragalin; avicularin; axillarin; baicalein; brazilin; brevifolin carboxylic acid; caryophyllene; chrysin-5,7-dihydroxyflavone; chrysoeriol; chrysosplenol; chrysosplenoside-a; chrysosplenoside-d; cosmosiin; δ-cadinene; dimethylmussaenoside; diacerylcirsimaritin; diosmetin; dosmetin; ellagic acid; ebinin; ethyl brevifolin carboxylate; flavocannibiside; flavosativaside; genistein; gossypetin-8-glucoside; haematoxylin; hesperidine; hispiduloside; hyperin; indole; iridine; isoliquiritigenin; isoliquiritin; isoquercitrin; jionoside; juglanin; kaempferol-3-rhamnoside; kaempferol-3-neohesperidoside; kolaviron; licuraside; linariin; linarin; lonicerin; luteolin; luetolin-7-glucoside; luteolin-7-glucoside; luetolin-7-glucoronide; macrocarpal-a; macrocarpal-b; macrocarpal-d; macrocarpal-g; maniflavone; methy scutellarein; naringenin; naringin; nelumboside; nepetin; nepetrin; nerolidol; oxyayanin-a; pectolinarigenin; pectolinarin; quercetagetin; quercetin; quercimertrin; quercitrin; quercitryl-2" acetate; reynoutrin; rhamnetin; rhoifolin; rutin; scutellarein; sideritoflavone; sophoricoside; sorbarin; spiraeoside; trifolin; vitexin; and wogonin.

The most preferred flavonoids and/or flavonoid derivatives are quercetin, quercetrin, myricetin, kaempferol and myrecetrin since these compounds may have some anti-inflammatory activity and/or may help stabilize cell membranes in combination with a relatively low toxicity, both of which activities may be beneficial in the treatment of radiation. Also, pharmaceutically acceptable salts of these flavonoids and/or flavonoid derivatives may be employed. The particular flavonoids and/or flavonoid derivative included in the composition may be determined by factors such as toxicity, bioavailability, solubility or dispersability, among others.

The particular flavonoids and/or flavonoid derivatives mentioned above are also preferred since some of these compounds may provide additional beneficial effects in the composition of the present invention. For example, quercetin may also have an antioxidative and anticlastogentic effect. It may prevent the decrease of endogenous ascorbic acid (vitamin C) in bone marrow after gamma-ray irradiation. In addition, some of the flavonoids and flavonoid derivatives may act as a radical scavenger to scavenge free radicals such as hydroxyl radicals to enhance their radioprotective effects.

In a more preferred embodiment, both quercetin and ascorbyl palmitate are included in the composition of the present invention because there seems to be an enhanced antioxidant effect of the combination of quercetin and ascorbyl palmitate.

The flavonoids and/or flavonoid derivatives are used in an amount of about 0.02 to about 2 grams per gram of the total antioxidant in the composition. More preferably, the flavonoids and/or flavonoid derivatives are employed in an amount of about 0.05 to about 1 gram, per gram of the total antioxidant in the composition, and, most preferably, the flavanoids and/or flavanoid derivatives are employed in an amount of 0.1 to about 0.4 grams per gram of the total antioxidant in the composition.

The composition of the present invention may further include selenium and/or a compound containing selenium. Selenium is known to be able to prolong the lifespan of a person exposed a severe dose of harmful radiation, e.g. as a result of the Chernobyl accident, and to reduce the potential occurrence of leukemia and other malignancies in that person. Selenium may be included in the composition of the present invention in such an amount that when the composition is administered to a human according to a method of the present invention, the daily dosage should be between 5 micrograms and 200 micrograms. Preferably, selenium may be included in the composition in such an amount that when the composition is administered to a human according to a method of the present invention, the daily dosage should be between 10 micrograms and 100 micrograms. An excessive amount of selenium and/or selenium compound in the composition of the present invention may render the composition toxic.

The oral and/or topical compositions of the present invention may further include an organic germanium compound such as carboxy ethyl sesquioxide of germanium or spirogermanuium. Organic germaniums are known to protect human cells from radiation damage. For example, controlled experiments have also shown that Ge-132 reduces mutations in *E. coli* due to γ-radiation by twenty-fold (see Mochizuki and Kada, *Antimutagenic effect of Ge-132 on γ-ray-induced mutations in E. coli B/r WP2 trp-*. 42(6) Int. J. Radiat. Biol, 653-59 (1982)). Germanium oxide has been shown to reduce the mutation rate in *Salmonella typhimurium* induced by Trp-P-2 (3-amino-1-methyl-5H-pyrido(4,3-b)indole), by 40-67 folds (see Kada, Mochizuki, and Miyao, *Antimutagenic Effects of Germanium Oxide on Trp-P-2 Induced Frameshift Mutations in Salmonella Typhimurium TA98 and TA* 1538, 125 Mutation Research, 145-51 (1984)). One or more organic germaniums may be included in the composition of the present invention in such an amount that when the composition is administered to a human according to a method of the present invention, the daily dosage of the germanium compound will be between 25 milligrams and 500 milligrams. Preferably, the organic germanium may be included in the composition in such an amount that when the composition is administered to a human according to a method of the present invention, the daily dosage of the germanium compound will be between 50 milligrams and 200 milligrams, and, most preferably, about 100 milligrams.

Alternatively, Siberian ginseng may be added to the oral and/or topical compositions of the present invention in the form of one or more of Siberian ginseng roots, Siberian ginseng powder, or extracts thereof which may contain one or more of the active ingredients of the Siberian ginseng. Siberian ginseng (*Eleutherococcus senticosus*) has been shown to have restorative effects on the functions of bone marrow damaged by exposure to radiation. The active ingredients of Siberian ginseng generally include eleutherosides A, B, B1, C, D and E; triterpenoid saponins; eleutherans A, B, C, D, E, F and G; and equivalents thereof. Siberian ginseng extract may be included in the composition of the present invention in such an amount that when the composition is administered to a human according to a method of the present invention, the daily dosage of the Siberian ginseng extract will be between 25 milligrams and 500 milligrams. Preferably, Siberian ginseng extract may be included in the composition in such an amount that when the composition is administered to a human according to a method of the present invention, the daily dosage of Siberian ginseng extract should be between 50 milligrams and 150 milligrams, and, most preferably, the daily dosage of the Siberian ginseng extract will be about 100 milligrams. If Siberian ginseng is used in a different form in the composition of the present invention, a skilled person should be able to adjust the amount being used accordingly based on the dosages for the Siberian ginseng extract given above.

Alternatively, the compositions of the present invention may include Korean ginseng (*panax ginseng*) and/or American ginseng (*panax quinquefolius*), in the form of roots, powder or an extract. Korean and/or American ginseng may prompt recovery of hemateikon and splenal weight and cause improvement of thrombocyte cells. This product is commercially available as Korea Insam. The daily dosage for Korean and/or American ginseng is the same as for Siberian ginseng. A skilled person is able to adjust the dosage of the Korean and/or American ginseng for different physical forms of administration, i.e. root, powder or extract. Of course, mixtures of one or more of Siberian ginseng, Korean ginseng and American ginseng and/or extracts of one or more of these ginseng types may also be employed.

Particularly preferred compositions in accordance with the present invention contain 3,800-4,800 IU of vitamin A palmitate; 2,400-7,200 IU of beta carotene; 240-480 IU vitamin $D_3$; 95-300 IU of vitamin E in the form of alpha-tocopherol; 48-72 mg of alpha-lipoic acid; 280-580 mg of quercetin, 120-240 mg of ascorbyl palmitate; 4.5-7.2 mg of curcumin; 4.5-10 mg of green tea (C&P); 45-100 mg of chlorophyllin; 24-100 mg of carboxy ethyl sesquioxide of germanium and 180-540 mcg of superoxide dismutase for every gram of non-carrier ingredients contained therein, wherein the non-carrier ingredients may include the compound that regulates cell differentiation and/or proliferation, the antioxidant, preferably, the flavonoids and/or flavonoid derivatives, and optionally selenium, organic germaniums and Siberian ginseng.

The composition in accordance with the present invention may provide one or more of the following beneficial effects to a patient when orally administered in an effective amount: antioxidant properties, free radical scavenging, transition metal chelation, nitric oxide stabilization, anti-inflammatory activity, relief of pain, burning, tingling, electrical sensations and/or hyperalgesia, increased microcirculation, nitric oxide stabilization, promotion of healing of skin ulcers and lesions, protein kinase C inhibition, decreased oxidative stress, anti-inflammation, protection against radiation damage, blockage of the formation of leukotrienes, stabilization of cell membranes, and regulation of cell differentiation, cell proliferation protection of mitochondrial membranes, reduction of cell damage, especially damage to DNA molecules, and plays a role in the repair and regeneration process of damages cells.

In one preferred embodiment, the compositions of the present invention may be formulated in any acceptable oral dosage forms including, but not limited to, capsules, tablets, lozenges, troches, hard candies, powders, sprays, elixirs, syrups, and suspensions or solutions.

The oral compositions of the present invention are preferably formulated with a pharmaceutically acceptable carrier. The pharmaceutically acceptable oral carrier may include, but is not limited to: (a) carbohydrates including fructose, sucrose, sugar, dextrose, starch, lactose, maltose, maltodextrins, corn syrup solids, honey solids, commercial tablet compositions including Emdex.RTM., Mor-Rex.RTM., Royal-T.RTM., Di-Pac.RTM., Sugar-Tab.RTM., Sweet-Rex.RTM., New-Tab.RTM., (b) sugar alcohols including mannitol, sorbitol, xylitol, and (c) various relatively insoluble excipients including dicalcium phosphate, calcium sulfate, calcium carbonate, microcrystalline cellulose and other pharmaceutical tableting ingredients.

In the case of tablets, for oral use, the pharmaceutically acceptable oral carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenges for oral use, the common pharmaceutically acceptable oral carrier may further include a binder such as PEG-8000. Preferably lozenges are made in a 0.1 to 15 grams size to allow a suitable dissolution rate for lozenges. More preferably lozenges are made in a 1 to 6 gram size to allow a suitable dissolution rate for lozenges. Dissolution time should be about 15 minutes in water bath testers at 37° C. degrees or about 30 minutes when orally dissolved as lozenges for treating a sore throat, congestion, laryngitis and mucous membrane inflammation.

To directly make compressible lozenges, add the active ingredients to PEG-8000 processed fructose; or add the active ingredient of the composition to crystalline fructose and commercially available, sweet, direct compression products such as Mendell's Sugartab.RTM., Sweetrex.RTM., or Emdex.RTM and add saccharin if desired, flavors as desired, glidants such as silica gel as needed, and lubricants such as magnesium stearate, as needed. The mixture should be kept dry and tableted soon after mixing. The ingredients are mixed and directly compressed into lozenges using conventional pharmaceutical mixing and tableting equipment. The compressive force is preferably sufficient to produce maximum hardness throughout the lozenges, to preserve the dissolution rate, and to maximize the efficacy of lozenges. Dissolution should occur over a sustained period of time of about 5 to 60 minutes, and preferably about 20 to 30 minutes. The composition should be stored in an airtight container and in a cool dark place. Tablets and troches can be manufactured using procedures similar to that described above with minor changes in the optional ingredients.

Alternatively, the oral composition of the present invention may be formulated in liquid form, such as syrups, mouthwashes or sprays with a solvent or dispersant such as water, or other liquids in a pharmaceutically acceptable oral carrier for delivery of the composition to a patient.

The oral composition may also be formulated in chewable compositions such as soft candy, gum drops, liquid filled candies, chewing gum bases and dental supplies, such as toothpastes and mouthwashes by further including fructose, sucrose, or saccharin in the composition, as needed.

The oral composition of the invention may be formulated in capsule form with or without diluents. For capsules, useful diluents include lactose and dried cornstarch. When suspensions are employed, emulsifying and/or suspending agents may be employed in the suspensions. In addition, solid compositions including one or more of the ingredients of the lozenges described above may be employed in soft and hard gelatin capsules.

The compositions of the present invention may also be formulated into a nasal aerosol or inhalant. Such compositions may be prepared using well-known techniques. For these types of formulations, suitable carriers may include the following ingredients: saline with one or more preservatives, absorption promoters to enhance bioavailability, fluorocarbons and/or other conventional solubilizing or dispersion agents.

Other materials, which may optionally be included in the oral composition of the present invention, include inositol, other B-complex vitamins, and anti-inflammatories. Also, ingredients such as sweeteners, flavorants, coloring agents, dyes, and diluents such as water, ethanol, propylene glycol, glycerin and various combinations thereof, may be included in the oral composition of the present invention.

The optional sweeteners which may be used in the oral composition of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the non-carrier ingredients of the oral composition.

The optional flavorants which may be used in the oral composition of the present invention include, but are not limited to, peppermint, peppermint-menthol, eucalyptol, wintergreen, licorice, clove, cinnamon, spearmint, cherry, lemon, orange, lime, menthol and various combinations thereof.

In general, the non-carrier ingredients described above, which may include the compound that regulates cell differentiation and/or proliferation, the antioxidant, preferably, the flavonoids and/or flavonoid derivatives, and optionally selenium, organic germanium, Korean ginseng, American ginseng and Siberian ginseng make up from about 0.5-50% by weight of the total composition. Preferably, the non-carrier ingredients will make up about 1-20% by weight of the total composition. More preferably, the non-carrier ingredients make up about 2-10% by weight of the total composition.

In a second preferred embodiment, the composition of the present invention is an oral composition, which includes a mixture of a compound that regulates cell differentiation and/or cell proliferation, an antioxidant and at least one other ingredient useful in the prevention, reduction or treatment of radiation injury. The at least one additional ingredient may be selected from flavonoids and/or flavonoid derivatives, selenium and/or selenium compounds, inositol, other B-complex vitamins, organic germanium, Korean ginseng, American ginseng, Siberian ginseng, extracts of one or more of these ginseng types and anti-inflammatories. These ingredients may be employed in the same relative amounts as given above.

In a second aspect, the present invention relates to a method of preventing, reducing or treating radiation injury by the oral administration of an amount of a composition, which includes a mixture of a compound that regulates cell differentiation and/or cell proliferation, and at least one antioxidant, which is effective to prevent, reduce or treat radiation injury.

In the preferred embodiment, the method of the present invention involves the oral administration of a composition to a human that may be potentially exposed to radiation, is in the process of being exposed to radiation, or has already been exposed to radiation. The effective amount of the oral composition to be administered will vary depending on such factors as the person being treated, the particular mode of administration, the activity of the particular non-carrier ingredients employed, the age, bodyweight, general health, sex and diet of the person, the time of administration, the rate of excretion, the particular combination of ingredients employed, the total content of the non-carrier ingredients of the oral composition, and the severity of the radiation injury or expected radiation exposure. It is within the skill of the person of ordinary skill in the art to account for these factors to provide a suitable dosage and treatment regimen for a standard 70 kg adult, described below.

As discussed above, the oral composition of the present invention may be administered to a patient in any orally acceptable dosage form including, but not limited to tablets, capsules, lozenges, troches, hard candies, powders, sprays, elixirs, syrups, and suspensions, solutions, mouthwashes, sprays with a solvent or dispersant such as water, or other liquids in a pharmaceutically acceptable oral carrier for delivery of the composition to a patient. The oral composition may also be formulated in chewable compositions such as soft candy, gum drops, liquid filled candies, chewing gum bases and dental supplies, such as toothpastes and mouthwashes by further including fructose, sucrose, or saccharin in the composition, as needed. The compositions of the present invention may also be formulated into a nasal aerosol or inhalant.

The oral composition may be administered 1-10 times per day, as needed, more preferably, 2-6 times per day, as needed, or most preferably, 3 times per day, to a person before, during and/or after radiation exposure. Preferably, during each administration of a dose, 1-5 tablets, capsules, lozenges, or equivalents thereof, are ingested by the person. More preferably, 1-2 tablets, capsules, lozenges or equivalents thereof are ingested by the person during each administration of a dose. Most preferably, the tablets, capsules or lozenges or equivalents thereof are ingested with a fluid such as water, juice, milk, or other suitable fluids.

Preferably, an effective amount of the composition for each administration contains 0.1 gram to 1 gram of the non-carrier ingredients, including, but not limited to, a compound that regulates cell differentiation and/or cell proliferation, and an antioxidant. Preferably, one or more of the flavonoids and/or flavonoid derivatives and/or at least one of selenium and selenium compounds are also included in the composition for oral administration as non-carrier ingredients. More preferably, an effective amount of the composition for each administration contains 0.2 gram to 0.5 gram of the non-carrier ingredients.

In a more preferred embodiment, the method of the present invention further includes the step of topically applying a composition which includes a mixture of a compound that regulates cell differentiation and/or cell proliferation, an antioxidant and a pharmaceutically acceptable topical carrier to an area of the skin prior to, during or after exposure of that area of skin to radiation. In the method, an effective amount of the topical composition of the invention is applied to the skin one to six times daily, as needed.

For prevention or reduction of radiation injury, the topical composition is preferably applied to the skin before potential exposure to radiation. More preferably, the topical composition of the present invention is applied to the skin at least once twenty-four hours before the start of the potential radiation exposure, and three times (e.g., morning, noon and bedtime) in the 24-hour period immediately before the potential radiation exposure. For each application, it is preferable to apply an amount of the composition, which is sufficient to cover the area of the skin to be potentially exposed to radiation with a thin layer of the topical composition. The topical composition should preferably be rubbed into the skin until little or no residue remains on the skin.

In a method for treating or reducing radiation injury, an effective amount of the topical composition of the invention is applied one to six times daily, as needed, to an area of skin inflicted with radiation injury during and/or after radiation exposure. In the method, a thin layer of the topical composition is preferably applied to the inflicted area of skin, as needed, and the topical composition should preferably be rubbed into the skin until little or no residue remains on the skin.

The method of the present invention, which employs combined oral and topical administration may provide one or more of the beneficial effects described above for the compositions of the invention. In addition, the method of the present invention may provide one or more additional beneficial effects due to one or more of the ingredients contained in the pharmaceutically acceptable oral or topical carriers as described above.

The pharmaceutically acceptable topical carrier used in the present invention may be a carrier suitable for use as a carrier for topical compositions. The non-carrier ingredients, which may include a compound that regulates cell differentiation and/or cell proliferation, an antioxidant, and optionally one or more flavonoids and/or flavonoid derivatives, selenium and/or a selenium compound, as well as inositol, other B-complex vitamins, and anti-inflammatories such as γ-linolenic acid, are dissolved, dispersed and/or suspended in the topical composition. Exemplary topical earners may include creams, ointments, lotions, pastes, jellies, sprays, aerosols, bath oils, and other topical pharmaceutical carriers, which accomplish direct contact between the active ingredients of the topical composition of the present invention and the pore of the skin. Preferably, the pharmaceutically acceptable topical carrier may make up more than about 80%, and more preferably about 80-95% w/w of the total composition. In some cases, it may be necessary to dissolve one or more the active ingredients in an appropriate solvent such as ethanol or DMSO (dimethylsulfoxide), and the like, to facilitate the incorporation of the one or more active ingredients into the topical composition or the pharmaceutically acceptable topical carrier.

One preferred topical carrier useful in the present invention may contain at least a hydrophilic ointment base, panthenol or a panthenol derivative and a dispersant if needed to disperse one or more insoluble or partially insoluble active ingredients in the carrier. Another preferred topical carrier of the present invention employs hydroxymethyl cellulose as the base and may contain ingredients contained in the carrier described below other than the hydrophilic ointment base.

Yet another preferred pharmaceutically acceptable topical carrier may include a solution of an acrylic copolymer in a non-aqueous solvent system, which mainly contains polyethylene glycol such as methoxy polyethylene glycol 550 (MPEG). A particular preferred MPEG is SENTRY CARBOWAX MPEG 550 sold by Union Carbide, which is a food/pharmaceutical/cosmetic grade material. Polyethylene glycols are generally non-toxic, water-soluble polymers that are fully biodegradable. In the solution, the acrylic copolymer would preferably be present in a concentration range of 3-6% by weight. Preferably, the acrylic copolymer has a molecular weight of more than 20,000. More preferably, the acrylic copolymer has a molecular weight of more than 100,000 so that it will not be systematically absorbed by the human body or skin. Components of the carrier material described below, other than the hydrophilic ointment base may also be employed in this carrier material.

Suitable hydrophilic ointment bases are known to persons skilled in the art. Exemplary hydrophilic ointment bases suitable for use in the present invention are non-U.S.P. hydrophilic ointment bases such as those made by Fougera, Inc. Sufficient hydrophilic ointment base is employed to act as a topical carrier for the active or non-carrier ingredients of the topical composition. Typically, the hydrophilic ointment base will make up more than about 80% of the total composition, and more preferably about 80-95% of the composition is the hydrophilic ointment base. The hydrophilic ointment base functions as a topical carrier and enhances penetration into the skin. Similar proportions of the hydroxymethyl cellulose-based carrier or acrylic copolymer solution based carrier may also be employed.

The panthenol or panthenol derivatives useful in the present invention include at least D-panthenol, DL-panthenol and mixtures thereof. This component of the topical carrier has skin moisturizing properties and acts as a quick, deep penetrating component of the topical carrier that helps deliver the non-carrier ingredients through the skin to the area to be treated and may also impart a healing effect to damaged tissue. The amount of panthenol or panthenol derivative to be employed is from about 0.25 to about 10 weight percent, more preferably from about 0.5 to about 5 weight percent and most preferably from about 1 to about 2 weight percent, based on the total weight of the topical composition.

The topical carrier of the present invention may also include additional ingredients such as other carriers, moisturizers, humectants, emollients, dispersants, radiation blocking compounds, particularly UV-blockers, as well as other suitable materials that do not have a significant adverse effect on the activity of the topical composition. Preferred additional ingredients for inclusion in the topical carrier are sodium acid phosphate moisturizer, witch hazel extract, glycerine humectant, apricot kernal oil emollient, and corn oil dispersant.

The topical composition of the present invention may also be employed to facilitate wound healing, for the treatment of skin cancer and/or one or more symptoms thereof, or as a topical composition for protecting skin from the harmful effects of radiation, such as radiation breakdown or radiation recall dermatitis.

The topical composition of the present invention is preferably made by cold compounding. This may be an important feature of the invention if one or more of the compounds employed in the topical composition are sensitive to heat or other types of energy in which case the activity of the topical composition may be detrimentally affected as a result of the formulation of the topical compositions in another manner. Thus, the ingredients of the topical composition the present invention are preferably mixed together, without heating using a sufficient amount of the topical carrier to provide a substantially homogeneous cream or ointment. It may be necessary to dissolve, disperse or suspend one or more of the ingredients prior to cold compounding in order to ensure substantially homogeneous distribution of the non-carrier or active ingredients in the topical composition.

A preferred pharmaceutically acceptable topical carrier of the invention can be made using the following ingredients, all based on use of one pound of hydrophilic ointment base. 25-35 parts of a 50% aqueous solution of sodium acid phosphate moisturizing agent, 5-10 parts of D- or DL-panthenol, 5-10 parts of glycerine, 1-3 parts of apricot kernal oil and 10-20 parts of witch hazel extract. For a topical composition of the present invention, particularly preferred combinations of antioxidants, a flavonoid and a compound which regulates cell differentiation and/or cell proliferation for use in the present invention comprises or consists especially of 2-9 parts of a dispersion of vitamins A and $D_3$ in a corn oil base, 1-4 parts of quercetin, 1-4 parts of vitamin E acetate, 2-4 parts of ascorbyl palmitate and 0.25-2 parts of α-lipoic acid. Optionally, one or more of the optionally ingredients of the topical composition such as glycerin, witch hazel extract, vitamins A and E and/or the ascorbyl palmitate can be reduced or eliminated from a particular topical composition, if desirable, or larger amounts of one type of component, i.e. an antioxidant, can be employed while reducing the amount of another component of the same type or having a similar activity.

When the composition of the present invention is formulated into a topical composition, preferably, the vitamins A and $D_3$ used in the composition of the present invention may be formulated in a single corn oil dispersion. Generally, every cubic centimeter (cc) of the corn oil dispersion of vitamins A and $D_3$ used in the present invention may contain about 500,000 to about 2,000,000 IU of vitamin A and about 50,000 to about 200,000 IU of vitamin $D_3$. Preferably, every cc of the corn oil dispersion of vitamins A and $D_3$ used in the present invention may contain about 1,000,000 IU of vitamin A and about 100,000 IU of vitamin $D_3$.

In one preferred embodiment in order to formulate the compound that regulates cell differentiation and/or cell proliferation in the composition of the present invention, which may be administered to a patient topically, it may be advantageous to use a dispersant. Suitable dispersants are known to persons skilled in the art. A particularly suitable dispersant for the compound that regulates cell differentiation and/or cell proliferation is corn oil. Corn oil also has the advantage that it is a natural product. The amount of corn oil used is an amount sufficient to disperse the compound that regulates cell differentiation and/or cell proliferation.

When the composition is formulated into a topical composition, the antioxidant enzyme used in the present invention is preferably skin-absorbable. However, due to its solubility characteristics, vitamin A may need to be formulated in a suitable dispersant such as corn oil in much the same manner as vitamin $D_3$ as described above when the composition is formulated into a topical composition.

The invention will now be further illustrated by the following example.

EXAMPLE 1

An oral composition of the present invention is described in Table 1 below. These ingredients may be mixed with a suitable amount of a pharmaceutically acceptable oral carrier described as above to form, for example, tablets for oral administration.

TABLE 1

| Ingredient | Amount Employed |
| --- | --- |
| Vitamin A palmitate and $D_3$ in corn oil dispersion | 10,000 IU of Vitamin A |
| β-Carotene | 15,000 IU |
| Vitamin E | 400 IU |
| α-Lipoic acid | 150 mg |
| Quercetin | 1200 mg |
| Ascorbyl palmitate | 500 mg |
| Curcumin | 15 mg |

TABLE 1-continued

| Ingredient | Amount Employed |
| --- | --- |
| Green tea (C&P) | 20 mg |
| Chlorophyllin | 200 mg |
| Carboxy ethyl sesquioxide of germanium | 100 mg |
| Superoxide dismutase | 1,125 mcg |

This oral composition can be administered 1-5 times daily for the prevention, reduction or treatment of radiation injury prior to, during or after radiation exposure.

EXAMPLE 2

A topical composition including a mixture of an hydrophilic ointment base, sodium acid phosphate moisturizing agent, a witch hazel extract carrier, glycerine, apricot kernal oil and DL-panthenol, as the pharmaceutically acceptable carrier and vitamins A and $D_3$, ascorbyl palmitate, α-lipoic acid and vitamin E acetate as the active ingredients which have antioxidant properties and/or regulate cell differentiation and/or cell proliferation was prepared by cold compounding. The formulation of the topical composition is given in Table 2.

The topical composition was prepared by first placing the hydrophilic ointment base in a stainless steel bowl and mixing briskly until the ointment becomes creamy. Then, the sodium acid phosphate, panthenol, ascorbyl palmitate, glycerine, apricot kernal oil, vitamins A and $D_3$, quercetin, witch hazel extract, vitamin E acetate and α-lipoic acid were added in that order. After each ingredient was added, mixing was continued until all traces of dry ingredients disappeared and a substantially homogeneous mixture was obtained. The final color should be a consistent yellow and the cream should have the consistency of cake frosting. The mixture was then placed in a sterile container. All containers which contact the topical composition during mixing must also be sterilized with, for example, zephiran chloride or a Clorox solution such as betadine.

This composition was topically administered, under the supervision of a physician, to several patients a day before undergoing radiation therapy treatment. The administration of the topical composition was carried out by applying a thin film of the composition to the areas of the skin to be exposed to radiation. The topical composition was applied three times during that day in the morning, noon and at bedtime. All of the patients administered with the topical composition of the present invention experienced much less severe radiation dermatitis after radiation therapy than patients who were not treated with the topical composition of the invention. The effects noted by the patients included reductions in burning, irritation and redness in the areas of skin that were treated. This topical composition can also be administered in a combined treatment involving the oral administration of the composition of Example 1.

TABLE 2

| Ingredient | Amount Employed |
| --- | --- |
| Hydrophilic ointment base | 1 pound |
| 50% aqueous solution of Sodium acid phosphate | 25 cc |
| DL-panthenol | 5 cc |
| Glycerine | 5 cc |
| Apricot kernal oil | 3 cc |
| Witch hazel extract | 12 cc |
| α-Lipoic acid | 500 mg |

TABLE 2-continued

| Ingredient | Amount Employed |
| --- | --- |
| Vitamin E acetate | 2 cc |
| Vitamin A and $D_3$ dispersion in corn oil | 6 cc |
| Ascorbyl Palmitate | 2 grams |
| Quercetin | 2 grams |

EXAMPLE 3

Tables 3-7 below exemplify some alternative topical formulations, which may be employed in the method of the present invention without listing all of the ingredients in the pharmaceutically acceptable topical carrier. These alternative formulations may be prepared using the same procedure as described in Example 1.

TABLE 3

| Ingredient | Amount Employed |
| --- | --- |
| Ascorbyl Palmitate | 2 grams |
| Hesperidine | 2 grams |
| Rutin | 2 grams |
| Vitamin A and $D_3$ dispersion in corn oil | 3 cc |
| Vitamin E Acetate | 1 cc |
| DL Panthenol | 5 cc |

TABLE 4

| Ingredient | Amount Employed |
| --- | --- |
| Ascorbyl Palmitate | 2 grams |
| Ascorbyl Glucosamine | 1 gram |
| Luteolin | 4 grams |
| Vitamin A and $D_3$ dispersion in corn oil | 3 cc |
| Vitamin E acetate | 1 cc |
| DL Panthenol | 5 cc |

TABLE 5

| Ingredient | Amount Employed |
| --- | --- |
| Ascorbyl Glucosamine | 2 grams |
| Apigenin | 4 grams |
| Vitamin A and $D_3$ dispersion in corn oil | 3 cc |
| Vitamin B acetate | 1 cc |
| DL Panthenol | 5 cc |

TABLE 6

| Ingredient | Amount Employed |
| --- | --- |
| Ascorbyl Palmitate | 2 grams |
| γ-Linolenic acid | 500 mg |
| Rutin | 4 grams |
| Vitamin A and $D_3$ dispersion in corn oil | 3 cc |
| Vitamin E acetate | 1 cc |
| DL Panthenol | 5 cc |

TABLE 7

| Ingredient | Amount Employed |
| --- | --- |
| Ascorbyl Palmitate | 4 grams |
| Quercetin | 2 grams |

TABLE 7-continued

| Ingredient | Amount Employed |
| --- | --- |
| Coenzyme Q10 | 500 mg |
| α-Lipoic acid | 50 mg |
| Vitamin A and $D_3$ dispersion in corn oil | 3 cc |
| Vitamin E acetate | 1 cc |
| DL Panthenol | 5 cc |

The foregoing detailed description of the invention and examples are not intended to limit the scope of the invention in any way and should not be construed as limiting the scope of the invention. The scope of the invention is to be determined from the claims appended hereto.

What is claimed is:

1. A method for the reduction or treatment of radiation injury comprising the step of orally administering to a human prior to expected exposure to radiation, during exposure to radiation or after exposure to radiation, a composition which comprises an amount of one or more compounds selected from the group consisting of vitamin $D_3$, 1(S), 3(R)-dihydroxy-20(R)-(1-ethoxy-5-ethyl-5-hydroxy-2-heptyn-1-yl)-9, 10-seco-pregna-5(Z), 7(E), 10 (19)-triene, cholesterols, 7-dehydrocholestrol, 1, 25-dihydroxyvitamin $D_3$, and 25-hydroxycholecalciferol, calcitriol, and pharmaceutically acceptable salts thereof, which is effective, when administered orally, to inhibit at least one of cell differentiation and cell proliferation, and an effective amount of one or more antioxidants selected from the group consisting of α-lipoic acid, chlorophyllin, glutathione, and pharmaceutically acceptable salts of each of the foregoing antioxidants, and wherein the radiation injury results from one or more types of radiation selected from the group consisting of proton radiation, fluoroscopic radiation, alpha radiation, beta radiation and gamma radiation and the radiation injury is selected from radiation dermatitis, vomiting, bone marrow damage and intestinal damage.

2. A method as claimed in claim 1, wherein the compound that inhibits at least one of cell differentiation and cell proliferation is vitamin $D_3$.

3. A method as claimed in claim 1, wherein the one or more compounds that inhibit at least one of cell differentiation and cell proliferation are selected from the group consisting of: vitamin $D_3$, 1, 25-dihydroxyvitamin $D_3$, 1(S), 3(R)-dihydroxy-20(R)-(1-ethoxy-5-ethyl-5-hydroxy-2-heptyn-1-yl)-9, 10-seco-pregna-5(Z), 7(E), 10 (19)-triene, and pharmaceutically acceptable salts thereof.

4. A method as claimed in claim 1, wherein the one or more antioxidants are selected from the group consisting of: α-lipoic acid, chlorophyllin, and pharmaceutically acceptable salts thereof.

5. A method as claimed in claim 1, wherein the compound that inhibits at least one of cell differentiation and cell proliferation is vitamin $D_3$, and the antioxidant is α-lipoic acid and chlorophyllin.

6. A method as claimed in claim 1, wherein the composition further comprises at least one flavonoid or flavonoid derivative selected from the group consisting of:

1,2,3,6-tetra-o-gallyol-β-d-glucose; 2'o-acetylacetoside; 3,3',4-tri-o-methyl-ellagic acid; 6,3',4'-trihydroxy-5,7,8-trimethoxyflavone; 6-hydroxy-luteolin; 6-hydroxy-kaempferol-3,6-dimethyl ether; 7-o-acetyl-8-epi-loganic acid; acacetin; acetoside; acetyl trisulfate quercetin; amentoflavone; apigenin; apiin; astragalin; avicularin; axillarin; baicalein; brazilin; brevifolin carboxylic acid; caryophyllene; chrysin-5,7-dihydroxyflavone; chrysoeriol; chrysosplenol; chrysosplenoside-a; chrysosplenoside-d; cosmosiin; δ-cadinene; dimethylmussaenoside; diacerylcirsimaritin; diosmetin; dosmetin; ellagic acid; ebinin; ethyl brevifolin carboxylate; flavocannibiside; flavosativaside; genistein; gossypetin-8-glucoside; haematoxylin; hesperidine; hispiduloside; hyperin; indole; iridine; isoliquiritigenin; isoliquiritin; isoquercitrin; jionoside; juglanin; kaempferol-3-rhamnoside; kaempferol-3-neohesperidoside; kolaviron; licuraside; linariin; unarm; lonicerin; luteolin; luetolin-7-glucoside; luteolin-7-glucoside; luetolin-7-glucoronide; macrocarpal-a; macrocarpal-b; macrocarpal-d; macrocarpal-g; maniflavone; methy scutellarein; naringenin; naringin; nelumboside; nepetin; nepetrin; nerolidol; oxyayanin-a; pectolinarigenin; pectolinarin; quercetagetin; quercetin; quercimertrin; quercitrin; quercitryl-2"acetate; reynoutrin; rhamnetin; rhoifolin; rutin; scutellarein; sideritoflavone; sophoricoside; sorbarin; spiraeoside; trifolin; vitexin; and wogonin.

7. A method as claimed in claim 6, wherein the flavonoids and flavonoid derivatives are selected from the group consisting of: quercetin, quercetrin, myricetin, kaempferol and myrecetrin.

8. A method as claimed in claim 1, wherein the composition further comprises selenium.

9. A method as claimed in claim 1, wherein the composition further comprises one or more ingredients selected from the group consisting of organic germanium, Korean ginseng, an extract of Korean ginseng, American ginseng, an extract of American ginseng, Siberian ginseng and an extract of Siberian ginseng.

10. A method as claimed in claim 1, wherein the composition further comprises one or more B-complex vitamins.

11. A method as claimed in claim 1, wherein a ratio of the amount of the compound that inhibits at least one of cell differentiation and cell proliferation to the amount of antioxidant is from about 200 IU per gram of antioxidant to about 3 million IU per gram of antioxidant.

12. A method as claimed in claim 1, wherein a ratio of the amount of the compound that inhibits at least one of cell differentiation and cell proliferation to the amount of antioxidant is from about 1800 IU per gram of antioxidant to about 1 million IU per gram of antioxidant.

13. A method as claimed in claim 1, wherein a ratio of the amount of the compound that inhibits at least one of cell differentiation and cell proliferation to the amount of antioxidant is from about 5000 IU per gram of antioxidant to about 200,000 IU per gram of antioxidant.

14. A method as claimed in claim 1 further comprising the step of applying to an area of skin before, during or after exposure to radiation, a topical composition which comprises an amount of one or more compounds that inhibit at least one of cell differentiation and cell proliferation which is effective, when administered topically in the topical composition, to inhibit at least one of cell differentiation and cell proliferation, and an effective amount of one or more antioxidants, formulated in a pharmaceutically acceptable topical carrier for a topical composition.

15. A method as claimed in claim 14, wherein the pharmaceutically acceptable topical carrier comprises a sufficient amount of at least one hydrophilic ointment base to form a topical composition.

16. A method as claimed in claim 15, wherein the pharmaceutically acceptable topical carrier further comprises a sufficient amount of a panthenol selected from D-panthenol and DL-panthenol to promote penetration of one or more of the antioxidants and compounds which inhibit at least one of cell differentiation and cell proliferation into the skin.

17. A method as claimed in claim 14, wherein the pharmaceutically acceptable topical carrier comprises hydroxymethyl cellulose.

18. A method as claimed in claim 14, wherein the pharmaceutically acceptable topical carrier comprises an acrylic copolymer dissolved in polyethylene glycol.

19. A method as claimed in claim 1, wherein the composition comprises vitamin $D_3$.

20. A method as claimed in claim 19, wherein the composition comprises chlorophyllin.

21. A method as claimed in claim 1, wherein the composition comprises α-lipoic acid.

22. A method as claimed in claim 20, wherein the composition comprises α-lipoic acid.

23. A method as claimed in claim 1, wherein the radiation injury is radiation dermatitis.

24. A method as claimed in claim 1, wherein the radiation injury is vomiting.

25. A method as claimed in claim 1, wherein the radiation injury is bone marrow damage.

26. A method as claimed in claim 1, wherein the radiation injury is intestinal damage.

* * * * *

UNITED STATES PATENT AND TRADEMARK OFFICE
CERTIFICATE OF CORRECTION

| | | |
|---|---|---|
| PATENT NO. | : 7,435,725 B2 | Page 1 of 1 |
| APPLICATION NO. | : 10/045790 | |
| DATED | : October 14, 2008 | |
| INVENTOR(S) | : Richard A. Rosenbloom | |

It is certified that error appears in the above-identified patent and that said Letters Patent is hereby corrected as shown below:

Claim 6, Column 19, line 10, please remove the word "unarm" and replace it with --linarin--.

Claim 6, Column 19, line 17, please place a space between "quercitryl-2"" and "acetate".

Signed and Sealed this

Sixteenth Day of December, 2008

JON W. DUDAS
*Director of the United States Patent and Trademark Office*